US008318092B2

(12) United States Patent
Reggiani et al.

(10) Patent No.: US 8,318,092 B2
(45) Date of Patent: Nov. 27, 2012

(54) OXYGENATOR WITH INTEGRATED ARTERIAL FILTER

(75) Inventors: Stefano Reggiani, Medolla (IT); Claudio Silvestri, Quarantoli Mirandola (IT); Alberto Giri, Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 130 days.

(21) Appl. No.: 12/770,327

(22) Filed: Apr. 29, 2010

(65) Prior Publication Data
US 2011/0268608 A1    Nov. 3, 2011

(51) Int. Cl.
*A61M 1/00*    (2006.01)
*A61M 37/00*    (2006.01)

(52) U.S. Cl. .............. 422/44; 422/45; 422/46; 422/47; 422/48; 604/4.01; 604/5.01; 604/6.09; 604/6.13; 604/6.14

(58) Field of Classification Search .............. 422/44–48; 604/4.01, 5.01, 6.09, 6.13, 6.14
See application file for complete search history.

(56) References Cited

U.S. PATENT DOCUMENTS

| | | | |
|---|---|---|---|
| 4,902,476 A | 2/1990 | Gordon et al. | |
| 5,192,439 A | 3/1993 | Roth et al. | |
| 5,514,095 A | 5/1996 | Brightbill et al. | |
| 5,578,267 A * | 11/1996 | Cosentino et al. | 422/46 |
| 5,817,278 A | 10/1998 | Fini et al. | |
| 5,830,370 A | 11/1998 | Maloney, Jr. et al. | |
| 6,113,782 A * | 9/2000 | Leonard | 210/321.89 |
| 6,241,945 B1 | 6/2001 | Owen | |
| 6,960,322 B2 * | 11/2005 | Stringer et al. | 422/45 |
| 2004/0175292 A1 | 9/2004 | Ghellil et al. | |
| 2007/0107884 A1 | 5/2007 | Sirkar et al. | |
| 2010/0272607 A1 | 10/2010 | Carpenter et al. | |
| 2011/0268609 A1 * | 11/2011 | Reggiani et al. | 422/46 |
| 2012/0046594 A1 | 2/2012 | Reggiani et al. | |
| 2012/0121463 A1 | 5/2012 | Reggiani et al. | |

FOREIGN PATENT DOCUMENTS

| | | |
|---|---|---|
| EP | 0312125 A1 | 4/1989 |
| EP | 0582959 A1 | 2/1994 |
| EP | 1108462 A2 | 6/2001 |
| EP | 1834656 B1 | 9/2007 |
| WO | WO9716213 A2 | 5/1997 |
| WO | WO9719714 A1 | 6/1997 |
| WO | WO9733636 A1 | 9/1997 |

OTHER PUBLICATIONS

European Search Report issued in EP Application No. 10173436, dated Feb. 14, 2011, 7 pages.
European Search Report issued in EP Application No. 10161451, dated Sep. 28, 2010, 5 pages.
European Search Report issued in EP Application No. 10186550, dated Jan. 27, 2011, 7 pages.
International Search Report issued in PCT/IB2011/054725, mailed Feb. 9, 2012, 12 pages.

\* cited by examiner

*Primary Examiner* — Leslie Deak
(74) *Attorney, Agent, or Firm* — Faegre Baker Daniels LLP

(57) ABSTRACT

An oxygenator combines, in a single structure, a heat exchanger, a gas exchanger and an arterial filter. Such an oxygenator permits fewer fluid connections and thus may simplify an extracorporeal blood circuit, including a heart-lung machine and a blood reservoir, in which it is used. In some cases, the oxygenator may be configured to include multiple purge ports for purging bubbles both before and after filtering the blood.

20 Claims, 7 Drawing Sheets

OXYGENATOR WITH INTEGRATED ARTERIAL FILTER

TECHNICAL FIELD

The disclosure pertains generally to arterial filters used in blood perfusion systems.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral, or other artery.

Often, an arterial filter is added to the extracorporeal circuit, after the oxygenator, as last barrier before the patient, so as to block any solid or gaseous emboli and prevent any such emboli from entering into the aorta of the patient. Recently, arterial filters integrated in the oxygenator have been developed, allowing the reduction of the priming volume of the circuit and decreasing the global haemodilution of the patient.

SUMMARY

According to an embodiment of the present invention, a blood processing apparatus includes an apparatus housing having a blood inlet and a blood outlet. The blood inlet may extend into an interior of the apparatus housing. A heat exchanger is in fluid communication with the blood inlet and is disposed about the blood inlet. A gas exchanger is disposed about the heat exchanger such that an inner surface of the gas exchanger is positioned to receive blood exiting an outer surface of the heat exchanger, an annular space being defined between an outer surface of the gas exchanger and an interior surface of the apparatus housing such that blood exiting the outer surface of the gas exchanger can collect in the annular space. An annular filter housing is arranged concentrically about the apparatus housing. A filter is arranged within the annular filter housing, forming a first annular chamber between the cylindrical filter and the apparatus housing and a second annular chamber between the cylindrical filter and the annular filter housing. An elongate opening is formed within the annular filter housing such that blood collecting in the annular space can pass into the first annular chamber. A first purge port is in communication with the first annular chamber and a second purge port is in communication with the second annular chamber.

According to another embodiment of the present invention, an integrated blood processing apparatus includes a housing having a blood inlet and a blood outlet, the blood inlet extending into an interior of the housing. A heat exchanger is disposed about the blood inlet and is in fluid communication with the blood inlet. An oxygenator is disposed about the heat exchanger and is in fluid communication with the heat exchanger. A filter housing defining an interior volume is secured to the housing. A filter is disposed within the filter housing, dividing the interior volume into a first chamber that is in fluid communication with the oxygenator and a second chamber that is in fluid communication with the blood outlet. A first purge port is in fluid communication with the first chamber and a second purge port is in fluid communication with the second chamber.

According to another embodiment of the present invention, an oxygenator includes an oxygenator housing having a blood inlet and a blood outlet. The oxygenator housing defines an oxygenator volume. An annular filter housing defining an interior filter volume is disposed about the oxygenator housing. A filter is disposed within the annular filter housing, dividing the interior filter volume into a first chamber that is in fluid communication with the oxygenator volume and a second chamber that is fluid communication with the blood outlet. A first purge port is disposed within a wall forming the annular filter housing and is in fluid communication with the first chamber. A second purge port is disposed within the wall forming the annular filter housing and is in fluid communication with the second chamber.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure pertains to a blood processing apparatus that combines, in a single structure, a heat exchanger, a gas exchanger or oxygenator and an arterial filter. In some embodiments, the term oxygenator may be used to refer to a structure that combines a heat exchanger, a gas exchanger and an arterial filter in a unitary device. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator.

In some embodiments, by combining the arterial filter with the oxygenator, the tubing set used to create the extracorporeal blood circuit may be reduced in complexity or number of parts and thus may simplify the extracorporeal blood circuit. In some embodiments, this will reduce the priming volume of the extracorporeal blood circuit.

Figure 1:
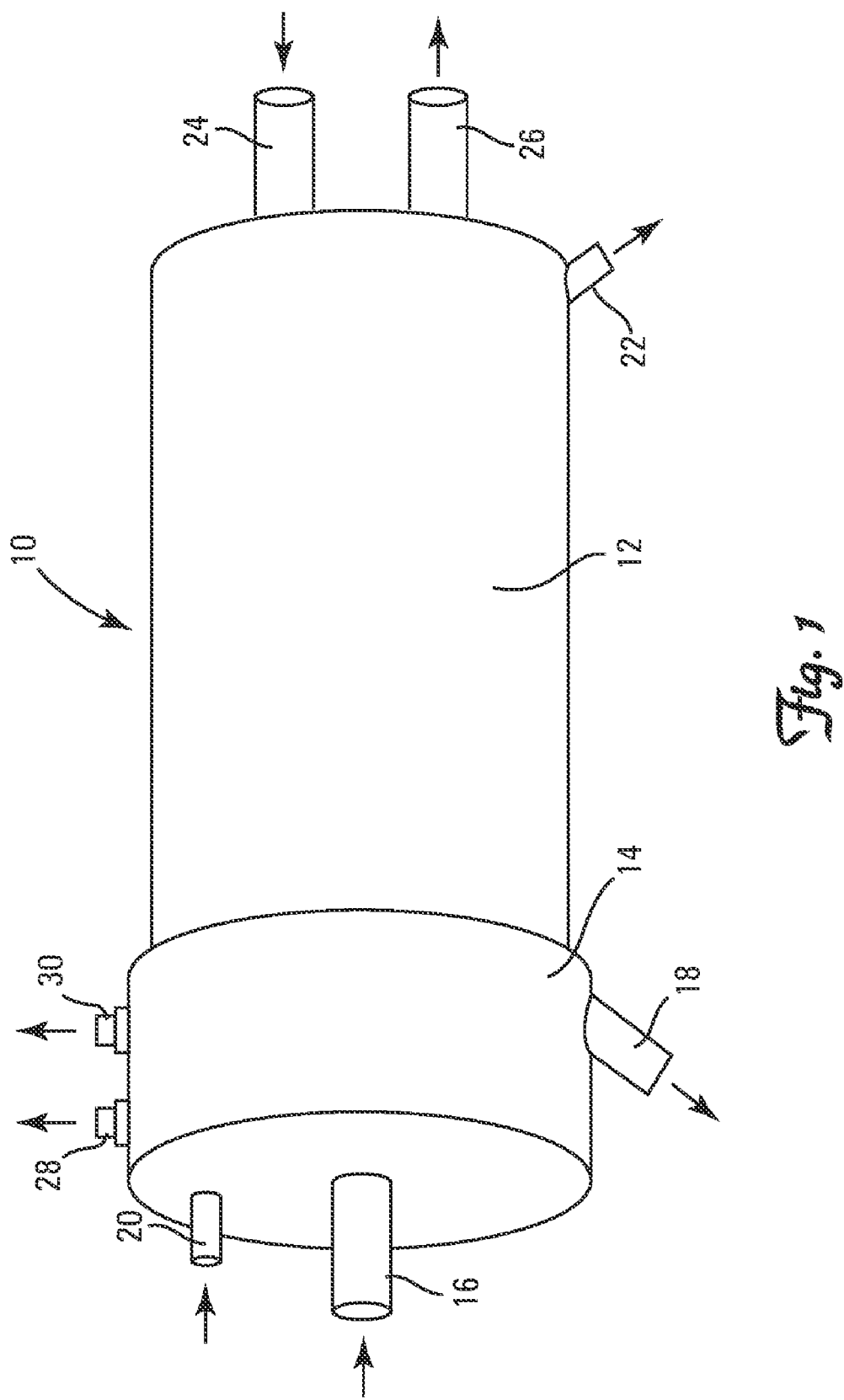
FIG. 1 is a schematic illustration of a blood processing apparatus including an integrated arterial filter in accordance with an embodiment of the invention.

FIG. 1 is a schematic illustration of a blood processing apparatus or oxygenator 10. While the internal components are not visible in this illustration, the oxygenator 10 may include one or more of a heat exchanger, a gas exchanger and an arterial filter. According to some embodiments, each of the heat exchanger, gas exchanger and arterial filter are integrated into a single structure that forms an oxygenator housing. The oxygenator 10 includes a device compartment or housing 12 and an arterial filter compartment or housing 14. In some embodiments, the arterial filter housing 14 may be integrally molded or otherwise structurally integrated with the device housing 12. In some cases, the arterial filter housing 14 may be separately formed and then secured or otherwise coupled to the device housing 12. According to various embodiments the heat exchanger, the gas exchanger, and the arterial filter housing 14 may have a cross-section shaped generally as a circle or as a parallelogram (e.g., a square or rectangle). Each of the heat exchanger, the gas exchanger and the arterial filter housing 14 may have generally the same sectional shape or each may have a different sectional shape.

In some embodiments, a blood inlet 16 extends through the arterial filter housing 14 and into the device housing 12. A blood outlet 18 exits the arterial filter housing 14. As noted, in some embodiments the oxygenator 10 includes a gas exchanger and thus may include a gas inlet 20 and a gas outlet 22. In some embodiments, the oxygenator 10 includes a heat exchanger and thus may include a heating fluid inlet 24 and a heating fluid outlet 26. As will be explained in greater detail with respect to FIG. 2, the oxygenator 10 includes a first purge port 28 and a second purge port 30. It is to be understood that the positions of the inlets, outlets and purge ports are merely illustrative, as other arrangements and configurations are contemplated. The purge ports may include a valve or a threaded cap. The purge ports operate to permit gases (e.g., air bubbles) that exit the blood to be vented or aspirated and removed from the oxygenator.

Figure 2:
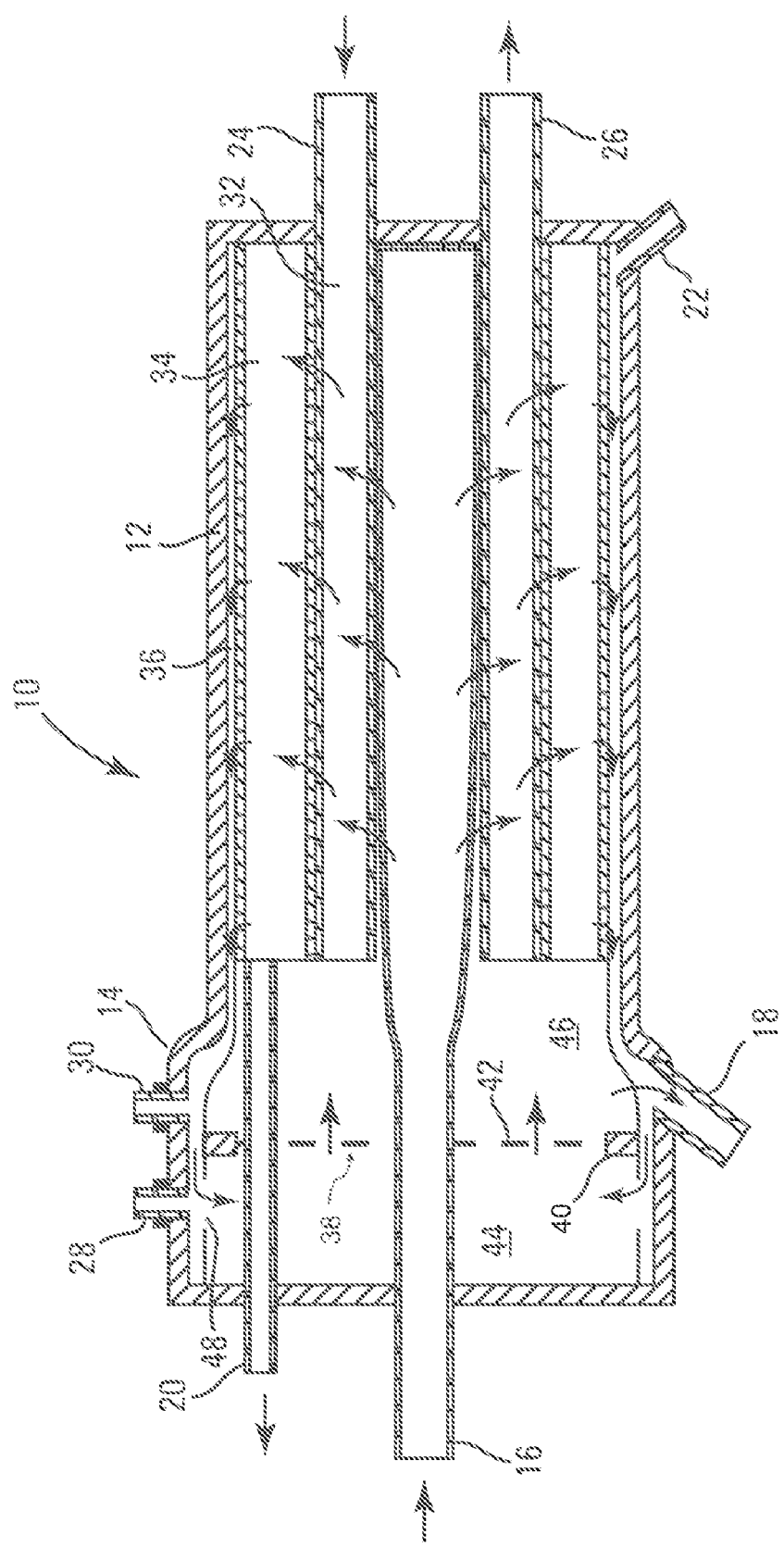
FIG. 2 is a cross-sectional illustration of the blood processing apparatus of FIG. 1.

FIG. 2 is a cross-sectional view of the oxygenator 10, illustrating internal components and an example of how blood can flow through the oxygenator 10. The oxygenator 10 includes a heat exchanger 32 and a gas exchanger 34. In some embodiments, the heat exchanger 32 includes a number of hollow fibers through which a heating fluid such as water can flow. The blood may flow around and past the hollow fibers and thus be suitably heated. In some embodiments, the hollow fibers may be polymeric. In some cases, metallic fibers may be used within the heat exchanger 32. According to other embodiments, the heat exchanger 32 includes a metal bellows or other structure comprising a substantial surface area (e.g., fins) for facilitating heat transfer with the blood.

In some embodiments the gas exchanger 34 may include a number of hollow fibers through which a gas such as oxygen may flow. The blood may flow around and past the hollow fibers. Due to concentration gradients, oxygen may diffuse through the hollow fibers into the blood while carbon dioxide may diffuse into the hollow fibers and out of the blood.

The oxygenator 10, according to some embodiments, includes an annular space 36 into which blood may flow as the blood exits the gas exchanger 34. As illustrated, the annular space 36 may extend into the arterial filter housing 14. According to exemplary embodiments, the annular space 16 may be generally circular or generally rectangular. The arterial filter housing 14 includes a filter 38. In some embodiments, the filter 38 includes an annular frame 40 and a net or mesh 42 spanning the annular frame 40. In some embodiments, the filter 38 may be considered as dividing a volume within the arterial filter housing 14 into a first chamber 44 and a second chamber 46. In various embodiments, the annular frame 40 and the net or mesh 42 are disposed concentrically with respect to the filter housing 14. In other embodiments the annular frame 40 and the mesh 42 are disposed about the housing 14 in a non-concentric manner. According to exemplary embodiments, the internal (i.e., priming) volume of the arterial filter housing 14 is between about 80 and about 110 mL. According to other embodiments, the priming volume is between about 90 and about 100 mL.

An opening 48 that may extend circumferentially up to about 360 degrees provides fluid communication between the annular space 36 and the first chamber 44. While blood is in the first chamber 44, any air bubbles that are present within the blood may be vented through the first purge port 28. Blood may pass through the filter 38 and into the second chamber 46. Any bubbles remaining in the blood, or caused by passage through the filter 38, may be vented through the second purge port 30. Blood may then exit the oxygenator 10 through the blood outlet 18. The presence of the first purge port 28 in the first chamber 44 and the second purge port 30 in the second chamber 46, according to various embodiments, will improve the priming speed due to the fact that bubbles present in the blood have both a first and a second opportunity to exit through a purge port. Moreover, in these embodiments, the efficacy of the bubble or gas removal is improved, again due to the fact that bubbles present in the blood have both a first and a second opportunity to exit through a purge port.

In some embodiments, the blood flow may be altered somewhat. For example, in some cases, the opening 48 may be positioned to provide fluid communication between the annular space 36 and the second chamber 46 while the blood outlet 18 is positioned in fluid communication with the first chamber 44. In some embodiments, the annular space 36 may empty directly into the second chamber 46, and may not extend into the first chamber 44.

Figure 3:
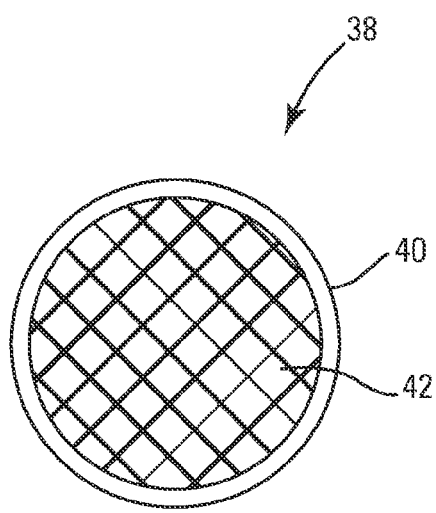
FIG. 3 is an illustrative view of a filter deployed within the blood processing apparatus of FIG. 1.
Figure 4:
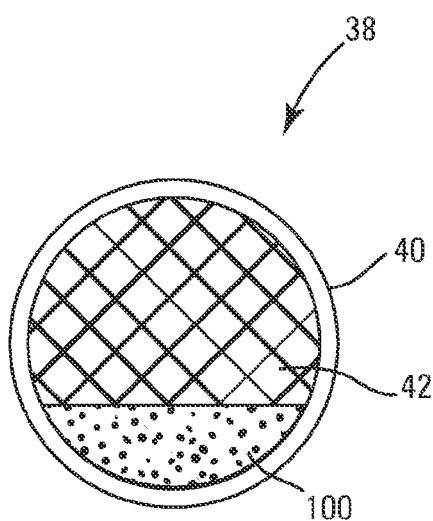
FIG. 4 is an illustrative view of another filter deployed within the blood processing apparatus of FIG. 1.

FIG. 3 is a view of the filter 38, illustrating the frame 40 and the net or mesh 42. FIG. 4 shows an embodiment of the filter 38 including a blocking plate 100. In some embodiments, the blocking plate 100 may be sized, shaped and positioned near the blood outlet 18 to limit preferential blood flow on the lower portion of the oxygenator 10. According to various embodiments, the filter 38 may have a cross-sectional shape that is circular, rectangular, or any other shape.

In some embodiments, the net or mesh 42 may have a mesh size that is the range of about 20 to about 200 microns. In some cases, the net or mesh 42 may have a mesh size of about 120 microns. In some instances, the net or mesh 42 may have a mesh size of from about 38-40 microns, and may be formed of a polymeric material such as polyester or polypropylene. In some cases, the net 42 may be coated with a biocompatible material. The blocking plate 100 may be formed of any suitable material. In some embodiments, the blocking plate 100 may be integrally formed with the frame 40. According to various exemplary embodiments, the net or mesh 42 has a surface area of between about 70 and about 90 square centimeters. According to other exemplary embodiments, the net or mesh 42 has a surface are of between about 75 and about 80 square centimeters.

Figure 5:
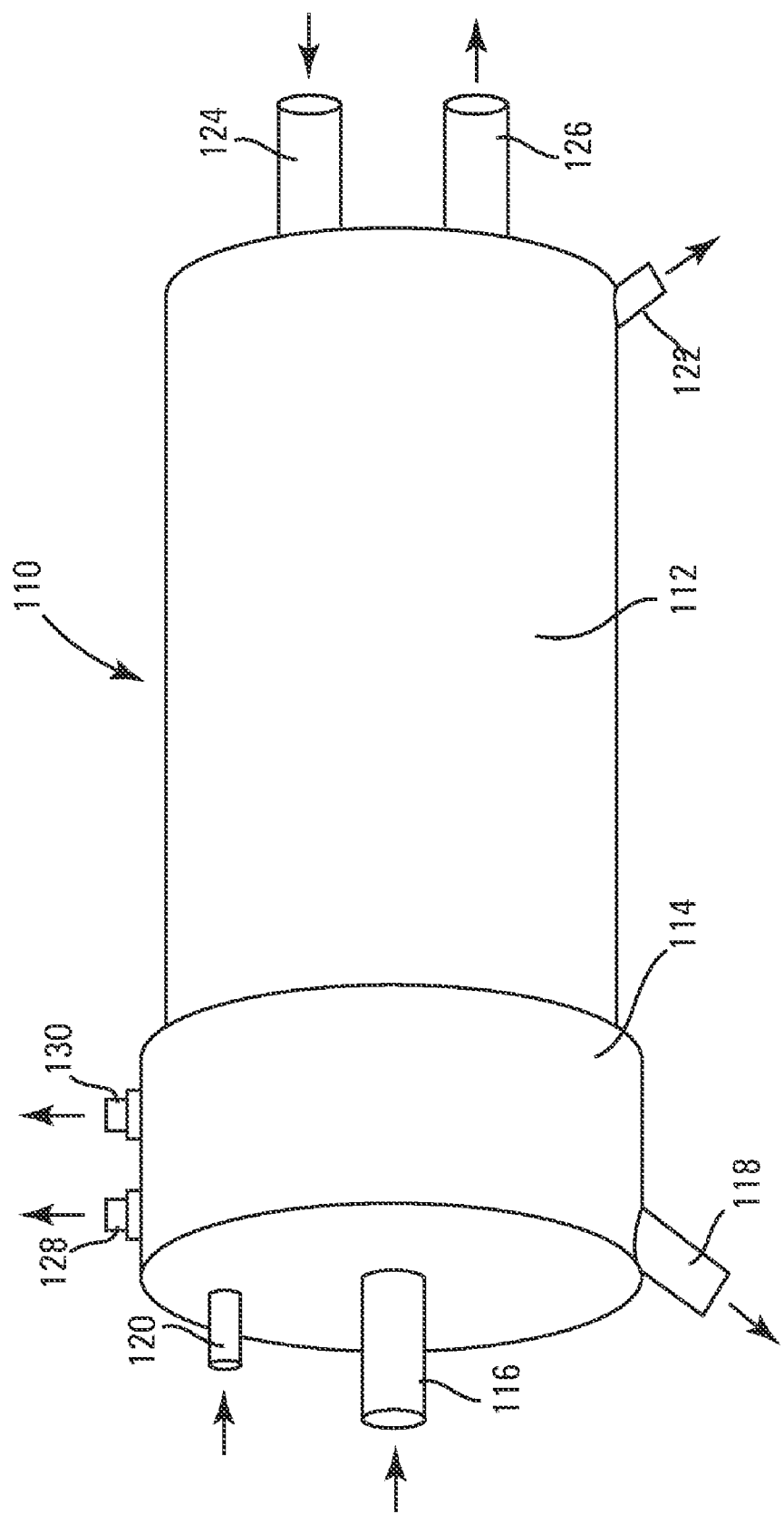
FIG. 5 is a schematic illustration of a blood processing apparatus including an integrated arterial filter in accordance with an embodiment of the invention.

FIG. 5 is a schematic illustration of a blood processing apparatus or oxygenator 110. While the internal components are not visible in this illustration, the oxygenator 110 may include one or more of a heat exchanger, a gas exchanger and an arterial filter. The oxygenator 110 includes a device housing 112 and an arterial filter housing 114. In some embodiments, the arterial filter housing 114 may be integrally molded or otherwise formed with the device housing 112. In some cases, the arterial filter housing 114 may be separately formed and then secured to the device housing 112.

In some embodiments, a blood inlet 116 extends through the arterial filter housing 114 and into the device housing 112. A blood outlet 118 exits the arterial filter housing 114. As noted, in some embodiments the oxygenator 110 includes a gas exchanger and thus may include a gas inlet 120 and a gas outlet 122. In some embodiments, the oxygenator 110 includes a heat exchanger and thus may include a heating fluid inlet 124 and a heating fluid outlet 126. As will be explained in greater detail with respect to FIG. 6, the oxygenator 110 includes a first purge port 128 and a second purge port 130. It is to be understood that the positions of the inlets, outlets and purge ports are merely illustrative, as other arrangements and configurations are contemplated.

Figure 6:
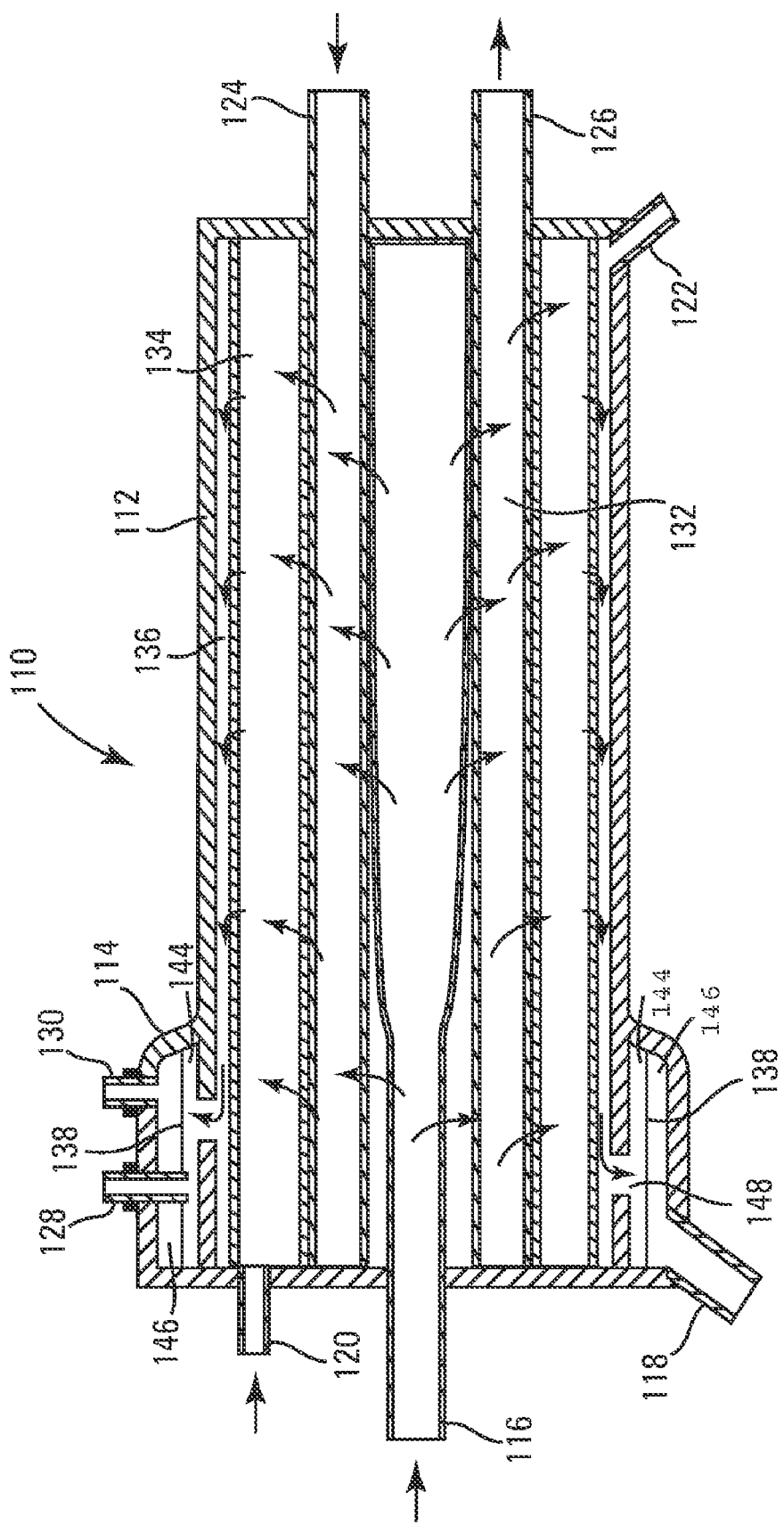
FIG. 6 is a schematic cross-sectional illustration of the blood processing apparatus of FIG. 5.

FIG. 6 is a cross-sectional view of the oxygenator 110, illustrating internal components and an example of how blood can flow through the oxygenator 110. The oxygenator 110 includes a heat exchanger 132 and a gas exchanger 134. In some embodiments, the heat exchanger 132 includes a number of hollow polymeric or metallic fibers through which a heating fluid such as water can flow. The blood may flow around and past the hollow fibers and thus be suitably heated. In some embodiments the gas exchanger 134 may include a number of hollow fibers through which a gas such as oxygen may flow. The blood may flow around and past the hollow fibers. Due to concentration gradients, oxygen may diffuse through the hollow fibers into the blood while carbon dioxide may diffuse into the hollow fibers and out of the blood.

As shown in FIG. 6, the gas exchanger is configured such that blood flows radially across the gas exchanger 134. In these embodiments, the oxygenator 110 includes an annular space 136 into which blood may flow as the blood exits the gas exchanger 134. According to various embodiments, the annular space 136 may be either open or it may be partially or completely filled with hollow fibers. As illustrated, the arterial filter housing 114 may extend over a portion of the annular space 136. According to other embodiments, the gas exchanger 134, the heat exchanger 132, or both may be configured such that blood is directed in a longitudinal flow path. In various exemplary embodiments where the gas exchanger 134 is configured such that blood flows in a longitudinal path, the annular space 136 is omitted. In these embodiments, the blood flows out of the gas exchanger 134 near an end and flows directly into the arterial filter housing 114. In some embodiments, the opening between the gas exchanger 134 and the arterial filter housing 114 is blocked or occluded at the radial location corresponding to the blood outlet 18 of the arterial filter housing 14, to minimize or prevent direct flow from the gas exchanger 134 into the blood outlet 18.

A filter 138 may be disposed within the arterial filter housing 114. In some instances, as illustrated, the filter 138 divides the space within the annular filter housing 114 into a first chamber 144 and a second chamber 146. An opening 148 that may extend circumferentially up to about 360 degrees provides fluid communication between the annular space 136 and the first chamber 144. While blood is in the first chamber 144, any air bubbles that are present within the blood may be vented through the first purge port 128. Blood may pass through the filter 138 and into the second chamber 146. Any bubbles remaining in the blood, or caused by passage through the filter 138, may be vented through the second purge port 138. Blood may then exit the oxygenator 110 through the blood outlet 118.

Figure 7:
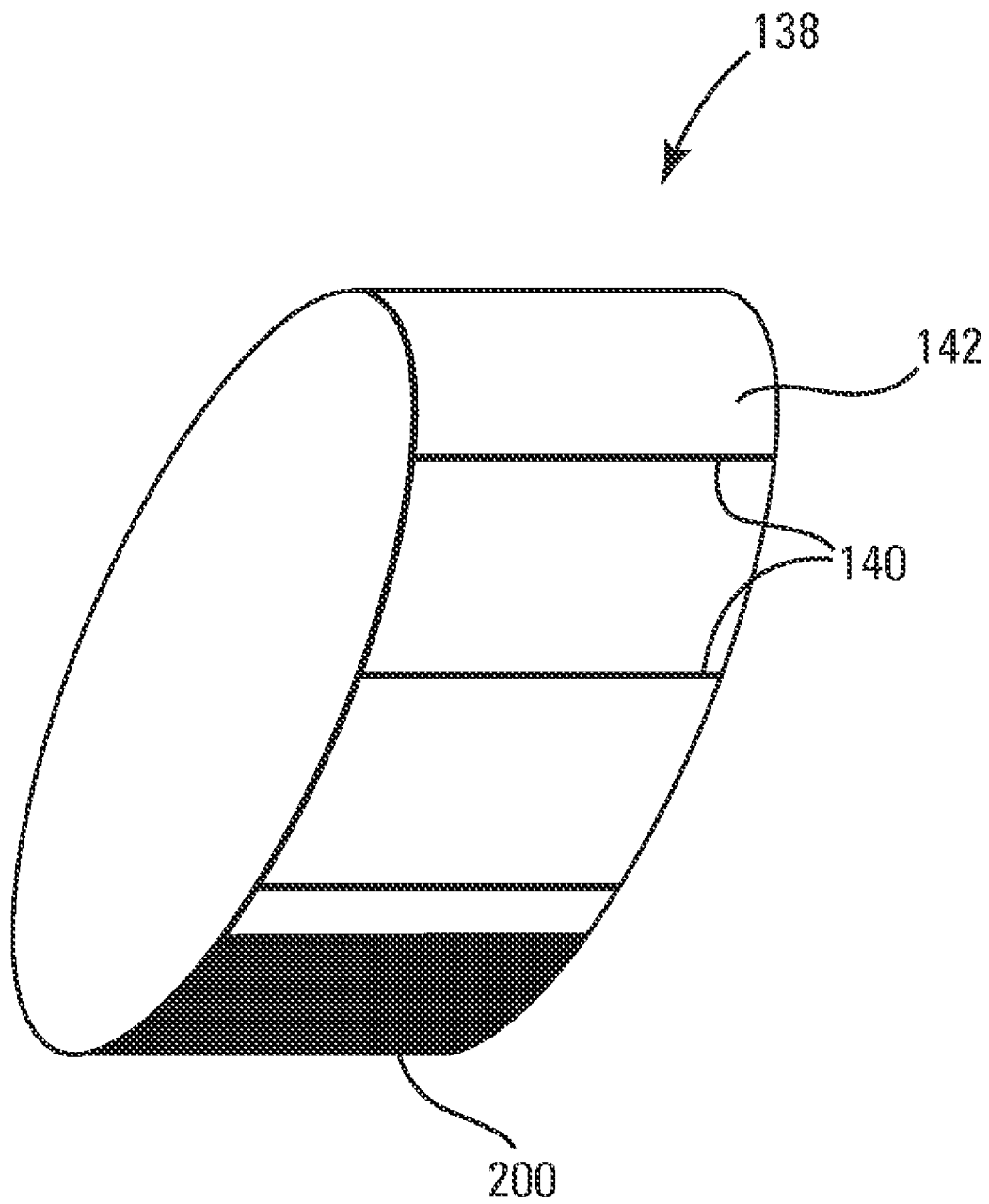
FIG. 7 is an illustrative view of a filter deployed within the blood processing apparatus of FIG. 5.

FIG. 7 is a view of the filter 138. In some embodiments, the filter 138 is a cylindrical filter that includes one or more reinforcements 140 and a cylindrical net or mesh 142. In some embodiments, the one or more reinforcements 140 may be molded into the cylindrical net or mesh 142. In some cases, the one or more reinforcements 140 may be adhesively secured to the cylindrical net or mesh 142. In some embodiments, the one or more reinforcements 140 may extend cylindrically about the filter 138. In some instances, the one or more reinforcements 140 may run across the filter 138.

In some embodiments, the net or mesh 142 may have a mesh size that is the range of about 20 to about 200 microns. In some cases, the net or mesh 142 may have a mesh size of about 120 microns. In some instances, the net or mesh 142 may have a mesh size of about 40 microns, and may be formed of a polymeric material such as polyester or polypropylene. In some cases, the net 142 may be coated with a biocompatible material.

In some embodiments, the net or mesh 142 may include a blocking region or plate 200 that is sized, shaped and positioned near the blood outlet 118 to limit preferential blood flow on the lower portion of the oxygenator 110. The blocking plate 200 may be formed of any suitable material. In some embodiments, the blocking plate 200 may be molded or otherwise formed within the net or mesh 142.

Figure 8:
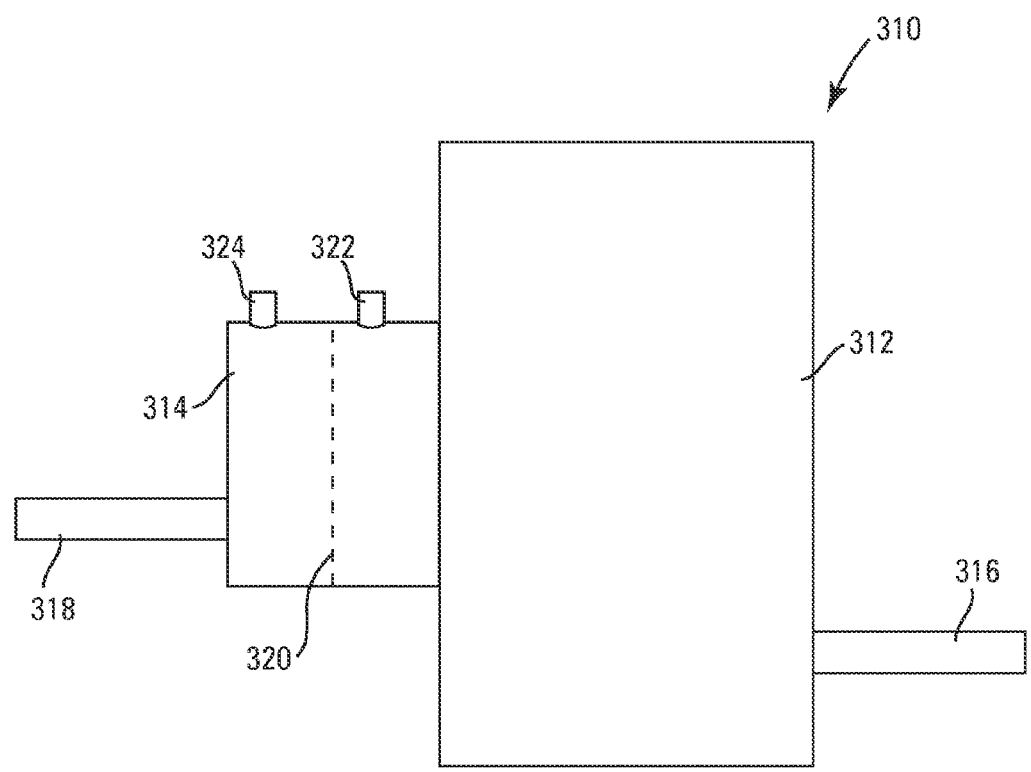
FIG. 8 is a schematic illustration of a blood processing apparatus including an integrated arterial filter in accordance with an embodiment of the invention.

FIG. 8 is a schematic illustration of a blood processing apparatus or oxygenator 310. While the internal components are not visible in this illustration, the oxygenator 310 may include one or more of a heat exchanger, a gas exchanger and an arterial filter. The oxygenator includes a device housing 312 and an arterial filter housing 314. In the illustrated embodiment, the arterial filter housing 314 is integrated into an end or side face of the device housing 312 and is configured such that blood exiting the device housing 312 enters the arterial filter housing 314. The device housing 312 includes a blood inlet 316 while the arterial filter housing 314 includes a blood outlet 318.

In some embodiments, as illustrated, the arterial filter housing 314 includes a net filter 320, a first purge port 322 and a second purge port 324. The first purge port 322 may be in fluid communication with an interior of the arterial filter housing 314 at a position upstream of the net filter 320 while the second purge port 324 may be in fluid communication with an interior of the arterial filter housing 314 at a position downstream of the net filter 320. As described in more detail above, this configuration allows an improvement and priming speed and efficacy, while also reducing the overall priming volume.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A blood processing apparatus comprising:
   an apparatus housing having a blood inlet and a blood outlet, the blood inlet extending into an interior of the apparatus housing;
   a heat exchanger in fluid communication with the blood inlet and disposed about the blood inlet;
   a gas exchanger disposed about the heat exchanger such that an inner surface of the gas exchanger is positioned to receive blood exiting an outer surface of the heat exchanger, an annular space being defined between an outer surface of the gas exchanger and an interior surface of the apparatus housing such that blood exiting the outer surface of the gas exchanger can collect in the annular space;
   an annular filter housing coupled concentrically about the apparatus housing, and including an outer portion;
   a filter comprising a planar net, arranged within the annular filter housing and encircling the apparatus housing, forming a first annular chamber between the filter and the apparatus housing and a second annular chamber between the filter and the outer portion of the annular filter housing, wherein the first annular and second annular chambers are co-radially arranged within the annular filter housing;
   an elongate opening formed within the annular filter housing such that blood collecting in the annular space can pass into the first annular chamber;
   a first purge port in communication with the first annular chamber; and
   a second purge port in communication with the second annular chamber.

2. The blood processing apparatus of claim 1, wherein bubbles within the blood can exit through the first purge port and/or the second purge port.

3. The blood processing apparatus of claim 1, wherein the heat exchanger is configured to permit water flow therethrough in order to heat the blood passing through the heat exchanger.

4. The blood processing apparatus of claim 1, wherein the gas exchanger is configured to permit gas to flow therethrough in order to add oxygen and remove carbon dioxide from the blood passing through the gas exchanger.

5. The blood processing apparatus of claim 1, wherein the heat exchanger comprises a cylindrical heat exchanger.

6. The blood processing apparatus of claim 1, wherein the gas exchanger comprises a cylindrical gas exchanger.

7. The blood processing apparatus of claim 1, wherein the blood inlet extends axially through the annular filter housing.

8. The blood processing apparatus of claim 1, wherein the filter comprises a cylindrical net having annular reinforcements.

9. The blood processing apparatus of claim 1, wherein the filter includes a biocompatible coating on the filter.

10. The blood processing apparatus of claim 1, wherein the first purge port extends through the filter such that the first purge port is in fluid communication with the first annular chamber.

11. An integrated blood processing apparatus comprising:
    a housing having a blood inlet and a blood outlet, the blood inlet extending into an interior of the housing;
    a heat exchanger disposed about the blood inlet, the heat exchanger being in fluid communication with the blood inlet;
    an oxygenator disposed about the heat exchanger, the oxygenator being in fluid communication with the heat exchanger;
    an annular filter housing disposed about and encircling the housing, the annular filter housing defining an interior volume;
    a filter comprising a planar net including longitudinal or annular reinforcements, disposed within the annular filter housing, the filter dividing the interior volume into an inner chamber in fluid communication with the oxygenator and an outer chamber in fluid communication with the blood outlet, wherein the inner and outer chambers are co-radially arranged within the annular filter housing;
    a first purge port in fluid communication with the inner chamber; and
    a second purge port in fluid communication with the outer chamber.

12. The integrated blood processing apparatus of claim 11, further comprising a heat exchanger fluid inlet and a heat exchanger fluid outlet, both in fluid communication with the heat exchanger.

13. The integrated blood processing apparatus of claim 11, further comprising a gas inlet and a gas outlet, both in fluid communication with the oxygenator.

14. The integrated blood processing apparatus of claim 11, wherein the filter comprises a polymeric net.

15. The integrated blood processing apparatus of claim 14, wherein the polymeric net comprises polyester or polypropylene.

16. The integrated blood processing apparatus of claim 11, wherein blood that enters the blood inlet passes through the heat exchanger, the oxygenator and the filter before exiting the blood processing apparatus through the blood outlet.

17. An oxygenator comprising:
    an oxygenator housing having a blood inlet and a blood outlet, the oxygenator housing defining an oxygenator volume;
    a filter compartment structurally integrated into the oxygenator housing and extending circumferentially around the oxygenator housing, the filter compartment defining an interior volume;
    a filter comprising a planar net including longitudinal or annular reinforcements, disposed within the filter compartment and encircling the oxygenator housing, the filter dividing the interior volume into an inner chamber in fluid communication with the oxygenator volume and an outer chamber in fluid communication with the blood outlet, wherein the inner and outer chambers are co-radially arranged within the filter compartment;
    a first purge port disposed within a wall forming the filter compartment, the first purge port in fluid communication with the inner chamber; and
    a second purge port disposed within the wall forming the filter housing, the second purge port in fluid communication with the outer chamber.

18. The oxygenator of claim 17, wherein the filter comprises a cylindrical net.

19. The oxygenator of claim 18, wherein the filter further comprises a plate disposed across a lower portion of the filter.

20. The oxygenator of claim 17, wherein the filter comprises a 40 micron mesh.

* * * * *